United States Patent [19]

Kaplan et al.

[11] Patent Number: 4,460,600
[45] Date of Patent: Jul. 17, 1984

[54] ADJACENTLY SUBSTITUTED KETAL DERIVATIVES OF CYCLOALKANE-AMIDE ANALGESICS

[75] Inventors: Lester J. Kaplan, Kalamazoo; Moses W. McMillan, Portage; Jacob Szmuszkovicz, Kalamazoo, all of Mich.

[73] Assignee: The Upjohn Company, Kalamazoo, Mich.

[21] Appl. No.: 439,104

[22] Filed: Nov. 4, 1982

Related U.S. Application Data

[63] Continuation-in-part of Ser. No. 252,536, Apr. 9, 1981, Pat. No. 4,359,476.

[51] Int. Cl.$^3$ .................. A61K 31/40; C07D 487/00
[52] U.S. Cl. .................................. 424/274; 560/250; 560/251; 560/255; 424/226; 424/267; 424/244; 424/301; 424/309; 424/311; 424/324; 548/578; 546/234; 260/239 A; 260/349; 564/162; 564/163; 564/164; 564/165; 564/166; 564/182; 564/183

[58] Field of Search .................. 548/578; 546/234; 260/239 A, 349; 564/162, 163, 164, 165, 166, 182, 183; 560/250, 251, 255; 424/226, 267, 274, 244, 301, 309, 324, 311

[56] References Cited

U.S. PATENT DOCUMENTS

| | | | |
|---|---|---|---|
| 3,510,492 | 5/1970 | Szmuszkovicz | 546/229 |
| 4,065,573 | 12/1977 | Lednicer | 424/278 |
| 4,098,904 | 7/1978 | Szmuszkovicz | 424/324 |
| 4,145,435 | 3/1979 | Szmuszkovicz | 424/274 |
| 4,212,878 | 7/1980 | Lednicer | 424/274 |
| 4,359,476 | 11/1982 | Kaplan et al. | 424/274 |

*Primary Examiner*—Jane T. Fan
*Attorney, Agent, or Firm*—John T. Reynolds

[57] ABSTRACT

Cis- and trans-N-[2-amino(adjacenty substituted bis(alkyloxy), bis(alkylthio), alkylthio or mercapto group substituted)-cycloaliphatic]benzeneacetamide and -benzamide compounds, e.g., ($\pm$)-(1$\alpha$,2$\beta$)-4-bromo-N-[3,3-dimethoxy-2-(1-pyrrolidinyl)cyclohexyl]-N-methylbenzamide, and salts thereof, are provided. These compounds have analgesic properties. Processes for their preparation are disclosed. Pharmaceutical compositions and methods of use are also provided.

10 Claims, No Drawings

ADJACENTLY SUBSTITUTED KETAL DERIVATIVES OF CYCLOALKANE-AMIDE ANALGESICS

CROSS REFERENCE

This is a continuation-in-part of application Serial Number 06/252,536, filed April 9, 1981, now U.S. Pat. No. 4,359,476, issued Nov. 16, 1982.

INTRODUCTION

This invention relates to N-[2-amino-bis(alkyloxy), mercapto, alkylthio- and bis(alkylthio)group substituted)cycloaliphatic]benzeneacetamide or -benzamide compounds. More particularly, this invention provides some new N-[2-amino(adjacently substituted bis(alkyloxy), bis(alkylthio), alkylthio- or mercapto group-substituted)cycloaliphatic]-benzeneacetamide and -benzamide compounds which have useful analgesic activity and low abuse liability. Processes for their preparation are disclosed. Pharmaceutical compositions and methods of use are also provided.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[2-(N',N'-dimethylamino)cyclohexyl]-N-methyl-2-(4-bromophenyl-)acetamide and trans-N-methyl-N-[2-(1-pyrrolidiny)cyclohexyl]-2-(3,4-dichlorophenyl)acetamide, which have potent analgesic activity; the preferred compounds thereof have, in addition, only low to moderate apparent physical dependence liability compared to morphine and methadone.

Also, Szmuszkovicz U.S. Pat. No. 4,098,904 discloses some cis- and trans-N-(2-aminocycloaliphatic)benzamide compounds, e.g., N-methyl-N-[2-aminocycloaliphatic]benzamide compounds, e.g., N-methyl-N-[2-(1-pyrrolidinyl)cyclohexyl]-3,4-dichlorobenzamide which have potent analgesic activity, amking them useful for relieving pain in warm-blooded animals.

Lednicer U.S. Pat. No. 4,212,878 discloses some N-[(1-amino-4-(mono- or di-oxygen group substituted)cyclohexyl)methyl]benzeneacetamide derivatives, e.g., 2-(3,4-dichlorophenyl)-N-[[8-(1-pyrrolidinyl)-1,4-dioxaspiro[4.5]dec-8-yl]methyl]acetamide, which also have analgesic drug properties with lower physical dependence liability characteristics than morphine or methadone. That Lednicer patent also refers to what is now Lednicer U.S. Pat. No. 4,065,573, which discloses some 4-amino-4-phenylcyclohexanone ketal compounds, e.g., 4-(m-hydroxyphenyl)-4-(dimethylamino)cyclohexanone ethylene ketal and 4-(m-hydroxyphenyl)-4-(n-butylmethylamino]cyclohexanone ethylene ketal, which are useful for relieving pain in animals, some of which compounds exhibit narcotic antagonist activity.

Those skilled in the art continue to search for new and more advantageous analgesic compounds.

More recently, in the above-identified cross-referenced application, we described and claimed some new 2-aminocycloaliphaticbenzeneacetamide and -benzamide compounds (Formula I) bearing oxy- or thio group substituents ($R_3R_4$) on a cycloaliphatic ring carbon adjacent to the nitrogen-bearing carbons of that cycloaliphatic ring, e.g., cis and trans-3,4-dichloro-N-methyl-N-[7-(1-pyrrolidinyl)-1,4-dioxaspiro[4.5]dec-6-yl]benzeneacetamide, and salts thereof, which were found to have useful ranges of analgesic properties while also having low apparent physical dependence liability properties. Those compounds were described by the general Formula I,
wherein R is hydrogen or $C_1$ to $C_3$-alkyl;
$R_1$ and $R_2$, taken separately, are each hydrogen or $C_1$ to $C_3$-alkyl;
$R_1$ and $R_2$, taken together with the nitrogen to which they are bonded are azetidinyl, pyrrolidinyl, or piperidinyl;
$R_3$, taken separately, is hydroxy, $C_1$ to $C_2$-alkyloxy or $C_1$ to $C_3$-alkanoyloxy;
$R_4$, taken separately, is hydrogen when $R_3$ is hydroxy, $C_1$ to $C_2$-alkyloxy, or $C_1$ to $C_3$-alkanoyloxy;
$R_3$ and $R_4$, taken together complete a moiety selected from the group, =G (oxo or thioxo), —G—$CH_2$$CH_2$—G—, —G—$CH_2CH_2CH_2$—G—, —G—$CH_2$CH—($CH_3$)$CH_2$—G—, —G$CH_2$C($CH_3$)$_2$$CH_2$G—, =N OH, and =N OC(=O)$CH_3$, wherein each G is oxygen or bivalent sulfur;
X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)$R_6$ wherein $R_6$ is hydrogen or $C_1$ to $C_2$-alkyl);
p and n are whole number integers selected from the group zero, 2, 3, or 4 such that one of p and n is always zero and the other of p and n is 2, 3 or 4;
q is zero or 1;
E is oxygen or bivalent sulfur;
provided that when R is $C_1$ to $C_3$-alkyl, $R_1$ and $R_2$, taken together with the nitrogen to which they are bonded complete a pyrrolidinyl ring, p is 3 and n is 0, q is 1, X and Y are chlorine in the 3 and 4 positions, $R_3$ is not hydroxy, $C_1$ and $C_2$-alkyloxy or $C_1$ to $C_3$-alkanoyloxy;
or a pharmaceutically acceptable salt thereof.

The above general Formula I compounds, particularly at the $R_3$ and $R_4$ substituent definitions, do not include the compounds of this invention.

OBJECTS OF THE INVENTION

It is an object of this invention to provide some new N-[2-aminoadjacently substituted-oxy- or thio-group-substituted cycloaliphatic]-benzeneacetamide and -benzamide compounds which are useful analgesic compounds.

Another object of the invention is to provide pharmaceutical compositions, useful in pharmaceutically effective dosage unit form for alleviating pain in warm-blooded mammals comprising compounds of Formula I in combination with a pharmaceutically acceptable carrier.

It is also an object of this invention to provide a method of alleviating pain in a warm-blooded mammal with the new compounds and compositions described herein.

Other objects, aspects and advantages of the invention will become apparent from reading the remaining specification and claims, which follow.

SUMMARY OF THE INVENTION

Briefly, this invention provides some new 2-aminocycloaliphaticbenzeneacetamide and -benzamide compounds bearing certain oxy- or thio- group substituents on a cycloaliphatic ring carbon atom adjacent to the nitrogen bearing carbons of that cycloaliphatic ring, e.g., 3,4-dichloro-N-[3,3-dimethoxy-2-(1-pyrrolidinyl)-cyclohexyl]-N-methylbenzeneacetamide, and salts thereof, which have useful ranges of analgesic properties while also having low apparent physical dependence liability and which also, hopefully, have reduced dysphoria inducing properties. This invention also includes pharmaceutical compositions containing these compounds as an active analgesic component and the method of inducing analgesic activity in an animal patient, including humans, by administering one of these new compounds in an amount effective and sufficient to induce analgesic activity, regardless of origin, e.g., traumatic pain, bone pain, cancer pain, post-surgical pain, homotopic pain, menstrual pain, headache, and the like. The invention also relates to new compounds in pharmaceutical dosage unit forms to be used, hopefully more advantageously, for the relief of pain in valuable animals and human patients suffering pain.

The invention also includes a method of treating pain in a human or valuable animal mammalian patient by administering to the patient suffering pain an amount of one of these compounds effective to alleviate or minimize such pain.

DETAILED DESCRIPTION OF THE INVENTION

More particularly, this invention provides some new compounds having a chemical structure of Formula I wherein p and n are each integers independently selected from the group 0, 2, 3 and 4 so that the resulting cycloaliphatic ring of Formula I has from 5 to 7 ring carbon atoms, inclusive, and the $R_3$ and $R_4$ bearing carbon is adjacent to one of the two nitrogen bearing carbons of that cycloaliphatic ring.

In detail, the compounds of this invention are those of Formula I wherein

R is hydrogen or $C_1$ to $C_3$-alkyl;

$R_1$ and $R_2$, taken separately, are each hydrogen or $C_1$ to $C_3$-alkyl;

$R_1$ and $R_2$, taken together with the nitrogen to which they are bonded are azetidinyl, pyrrolidinyl or piperidinyl;

$R_3$, taken separately, is hydrogen;

$R_4$, taken separately, is mercapto (—SH), —S($C_1$ to $C_3$—alkyl), or $R_3$ is —$GR_5$ when $R_4$ is —$GR_5$;

each G is oxygen or bivalent sulfur, and both G moieties are the same in any one compound;

$R_5$ is $C_1$ to $C_2$-alkyl;

X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino (—NHC(=O)$R_6$ is hydrogen or $C_1$ to $C_2$-alkyl);

p and n are whole number integers selected from the group zero, 2, 3 or 4 such that one of p and n is always zero and the other of p and n is 2, 3 or 4;

q is zero or 1;

E is oxygen or bivalent sulfur;

or a pharmaceutically acceptable salt thereof.

Thus, these compounds are described so that the new oxy or thio-group substituent(s) ($R_3$ and $R_4$) are bonded to a cycloaliphatic ring carbon atom which is ajacent to the ring carbon atom bearing the amido-nitrogen or amino-nitrogen of the compounds.

The compounds of Formula I or their acid addition salts in their crystalline state may sometimes be isolated from their reaction mixtures as solvates, i.e., with a discrete quantity of solvent, e.g., water, ethyl acetate, methanol, and the like, associated physically, and thus not effecting the chemical entity per se.

It will be recognized by those in the organic chemical art that the carbon atoms at positions 1 and 2 of the cycloaliphatic ring of structure (I) to which nitrogens are bonded are asymmetrically substituted. Likewise, for certain definitions of $R_3$ and $R_4$, the cycloaliphatic ring carbon atom to which $R_3$ and $R_4$ are bonded may also be asymmetrically substituted. Each of these three carbon atoms can independently possess an R or S-configuration and thus a compound of the formula (I) may have as many as $2^3$ or 8 stereoisomers which comprise four pairs of enantiomers; each enantiomeric pair is termed a racemate. See, for example, J. B. Henderickson, D. J. Cram, and G. S. Hammond, Organic Chemistry, Third Edition, McGraw-Hill Book Company, New York, N.Y., 1970, pages 198–230, particularly pages 207, 208, 213, 215. Of the four racemates, two will have the nitrogen-containing groups at positions 1 and 2 of structure (I) in a trans orientation: that is, the groups will be on opposite sides of the plane of the cycloaliphatic ring; such compounds will be generally referred to in this specification as trans compounds and are meant to include both possible configurations of the third substituted ring carbon if it is asymmetrically substituted. The other two racemates will have the nitrogen-containing groups at positions 1 and 2 of structure (I) in a cis orientation: that is, the groups will be on the same side of the cycloaliphatic ring; such compounds will be generally referred to in this specification as cis compounds and are meant to include both possible configurations of the third substituted ring carbon atom if it is asymmetrically substituted. The four racemates of structure (I) compounds can each exist as a mixture of the two enantiomers or each enantiomer of each pair can be separated by conventional methods. This invention includes within its scope all enantiomeric and diastereomeric forms of Formula I compounds either in pure form or as mixtures of enantiomers or diastereomers. In Charts A through I, when a particular enantiomer or diastereomer or set of enantiomers or diastereomers is illustrated, the intent is only to convey relative stereochemistry. When it is desired to specify for a formula (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972–1976)", a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of Formula I compounds is indicated by: (1) the arbitrary designation of 1α for the orientation of the substituent on (asymmetric) carbon atom number one; (2) the designation 2α or 2β when the substituent on (asymmetric) carbon atom number two is on the same or opposite side of the plane of the cycloaliphatic ring, respectively, relative to said $C_1$ substituent; and (3) the designation xα or xβ when the substituent on (asymmetric) carbon atom number x is on the same or opposite side of the plane of the cycloaliphatic ring, respectively, relative to said $C_1$ substituent.

Two isomers which differ only in the stereochemistry at one asymmetric carbon atom of the cycloaliphatic ring are sometimes herein referred to as epimers.

In the Formula I compounds, the halogens having atomic numbers of from 9 to 35 are fluorine, chlorine and bromine, the term "$C_1$ to $C_3$-alkyl" means methyl, ethyl, n-propyl and isopropyl, and allyl means 2-propen-1-yl.

A most preferred subgroup of these Formula I compounds are those wherein one of p and n is 0 and the other of p and n is 2, 3 or 4, so that the cycloaliphatic ring has 5 to 7 ring carbons, q is 0 or 1, and at least one of X and Y is a halogen having an atomic number of from 9 to 35 in the 3- or 4- positions or both of X and Y are halogens having an atomic number of from 9 to 35, one of X and Y being in the 3-position and the other of X and Y being in the 4-position of the phenyl ring; R is hydrogen or $C_1$ to $C_3$-alkyl; $R_1$ and $R_2$ are taken together with the nitrogen to which they are bonded to complete an azetidinyl, pyrrolidinyl or piperidinyl ring; and E is oxygen, $R_3$ and $R_4$ are each —$GR_5$ where each G is oxygen and $R_5$ is $C_1$ to $C_2$-alkyl;
and the pharmaceutically acceptable salts thereof.

Examples of compounds of this group include the cis and transioners of:
4-bromo-N-[3,3-dimethoxy-2-(1-pyrrolidinyl)cyclohexyl]-N-methylbenzeneacetamide,
3,4-dichloro-N-[6,6-dimethoxy-2-(1-pyrrolidinyl)cyclohexyl]-N-methylbenzeneacetamide,
4-bromo-N-[6,6-dimethoxy-2-(1-pyrrolidinyl)cyclohexyl]-N-methylbenzamide.
3,4-difluoro-N-[3,3-dimethoxy-2-(1-pyrrolidinyl)cyclohexyl]-N-methylbenzeneacetamide,
4-bromo-N-[6,6-diethoxy-2-(1-piperidinyl)cyclohexyl]-N-methylbenzamide,
3,4-dibromo-N-[3,3-dimethoxy-2-(1-pyrrolidinyl)cyclopentyl]-N-ethylbenzeneacetamide,
3-bromo-N-[7,7-diethoxy-2-(1-azetidinyl)cycloheptyl]-N-propylbenzamide,
3,4-dichloro-N-[3,3-dimethoxy-2-(1-pyrrolidinyl)cyclohexyl]-N-methylbenzeneacetamide, and the like, and the pharmacologically acceptable salts thereof.

The di-$C_1$ to $C_2$-alkyl ketals of this invention, that is, the compounds of Formula I wherein $R_3$ is —$GR_5$, $R_4$ is —$GR_5$ and each G is oxygen, can be prepared by reacting a ketone, such as is shown in Chart C, structure XXXVIII, or an analogous cis amino-amide ketone (See Chart F, structure LXVIIa; Chart G, structure LXXVIIIa) in methanol or ethanol as solvent in the presence of trimethylorthoformate or triethylorthoformate, respectively, and a suitable acid such as hydrochloric acid. The resulting reaction mixture is reacted at from 20° C. to reflux temperature for a time sufficient to form the desired dialkyl ketal compound (I); usually a reaction time of about 16 hours in refluxing methanol or ethanol is a sufficient reaction time. The solvent is then removed by evaporation and the dialkyl ketal product (I) is purified by conventional techniques such as recrystallization or chromatography.

The di-$C_1$-$C_2$-alkylthio ketals of this invention, that is, the compounds of the Formula (I) wherein $R_3$ is —$GR_5$, $R_4$ is $GR_5$ and each G is bivalent sulfur can be prepared by methods well known in the art as described generally in "Protective Groups in Organic Synthesis", T. W. Greene, John Wiley & Sons, New York, 1981, pp. 129-30. Thus, for example, a ketone of the Formula XXXVIII (CHART C) or an analogous cis ketone, (LXVIIa (Chart F) or LXXVIIIa (Chart G), is reacted with methyl or ethyl mercaptan in the presence of a suitable acid such as hydrochloric acid to form a dialkylthio ketal of this invention.

The mercaptans of this invention, that is, compounds of the general Formula (I) wherein $R_3$ is hydrogen and $R_4$ is —SH, are prepared by methods known in the art as described, for example, in "Comprehensive Organic Chemistry, The Synthesis and Reactions of Organic Compounds", Ed. D. Barton and W. D. Ollis, Volume 3 edited by D. N. Jones, Pergamon Press, New York, 1979, pp. 608. For example, a trans-alcohol of the formula XXII (Chart B) or an analogous cis alcohol (XLVIII, Chart D) can be converted to a para-toluenesulfonate derivative which is reacted with hydrogen sulfide to produce the desired thiol of this invention. An additional helpful literature reference is "The Chemistry of the Thiol Group" Part 1, Ed. S. Patai, John Wiley & Sons, New York, 1974, for example, pages 163, 164, 179, 180, 220.

The monoalkylthio compounds of this invention, that is, the compounds of general Formula (I) wherein $R_3$ is hydrogen and $R_4$ is —S—($C_1$-$C_2$-alkyl), are prepared by methods known in the art as described, for example in "Comprehensive Organic Chemistry", cited above, pages 36–39. For example, a thiol of this invention produced as described above, can be reacted with an appropriate $C_1$-$C_2$-alkyl halide, preferably bromide, to produce a monoalkylthio compound of this invention.

Throughout the synthetic procedures described herein, care must be taken that the groups X and Y are not undesirably altered by the reaction conditions. The use of protecting groups may be necessary as well known in the art.

In general, and with the exceptions noted below, the amino-amideketone starting materials can be prepared by a variety of process routes. Such compounds can be prepared by reacting the selected 1,2-cycloaliphatic diamine of the General Formula II wherein p, n, R, $R_1$, $R_2$ are as defined above, and $R_3$ and $R_4$ are taken together to denote a ketal substituent, e.g., —$OCH_2CH_2O$—, —$OCH_2CH_2CH_2O$—, —$OCH_2CH(CH_3)CH_2O$— or —$OCH_2C(CH_3)_2CH_2O$— with: (1) a suitable acyl source such as the appropriate acyl imidazole of Formula III (General Chemical Structure Chart) wherein q, E, X and Y are as defined above; or (2) with an acyl halide of Formula IV (General Chemical Structure Chart) wherein M is chloride or bromide, and q, E, X and Y are as defined above in the presence of an acid scavenger such as triethylamine; or (3) with a carboxylic acid of Formula V (General Chemical Structure Chart) in the presence of a condensing agent, such as a carbodiimide, wherein q, E, X and Y are as defined above, in an organic solvent for the reactants, preferably in an ether solvent such as diethyl ether or a cyclic ether solvent such as tetrahydrofuran (THF) or dioxane, or the like, until the amido-amide ketal compound, e.g., XXXVII (Chart C) is produced. This amino-amide ketal compound is then hydrolyzed with a suitable mineral acid such as sulfuric acid or the like to form the amino-amide ketone, e.g., XXXVIII (Chart C). Carbodiimides such as dicyclohexylcarbodiimide or diisopropylcarbodiimide are examples of such condensing agents.

The reactants (II) and (III) or (II) and (IV) or (II) and (V) can be mixed in substantially equimolar proportions to effect formation of the desired amino-amide-ketal, but in cases where the non-pertinent amino nitrogens are protected against reaction, if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process.

Exceptions—When the ketone starting material is to be one of Formula (I) wherein $R_3$ and $R_4$ together denote an oxo group, and wherein one or both of $R_1$ and $R_2$ is to be hydrogen, the amino-hydrogens in the $R_1$ and/or $R_2$ positions must first be protected by procedures known in the art, then the N-protected diamine reactant (IIa) wherein R, n and p are as defined for Formula II and each "—H—Q" denotes a protected amino hydrogen group, and $R_3$ and $R_4$ together denote an $-OCH_2CH_2O-$, $-OCH_2CH_2CH_2O-$, $-OCH_2CH(CH_3)CH_2O-$ or $-OCH_2C(CH_3)_2CH_2O-$ group, reacted with the selected acyl imidazole (III), or with the acyl halide (IV) or with the carboxylic acid (V) in the presence of a condensing agent, to form the N-[2-(N-protectedamino)ketal group-substituted cycloaliphatic]benzamide or benzeneacetamide, which is then treated to remove the N-protecting group and to hydrolyze the ketal group to the ketone to leave as product the desired N-[2-(amino)oxo group-substituted-cycloaliphatic]benzamide or -benzeneacetamide starting material.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the Formula (V) in an organic solvent. The carboxylic acids are either known in the art or are prepared by methods known in the art.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids, and the like. The reaction can be carried out in aqueous or organic liquid solvent or non-aqueous media such as diethyl ether, ethyl acetate, and the like. Non-aqueous media are preferred. When it is desired to obtain optically resolved products in crystalline form, it may be more convenient to form salts such as maleates, citrates or pamoates rather than the inorganic acid addition salts, such as the hydrochlorides. Also, whereas some acids, for example, oxalic acid, can be used to produce the amino-amide product in a more easily handled solid form, e.g., in plant manufacturing isolation procedures, it would preferably not be used as a pharmaceutically acceptable salt form of the amino-amide product.

Procedures for preparing the oxy-group substituted diamines (II) and amino-amide-oxy compounds useful for preparing the compounds of this invention are summarized by the reaction Charts A through I.

In these Charts, R, $R_1$, $R_2$, n, p, q, E, X and Y are as defined above;
A is $-CH_2CH_2-$, $-CH_2CH_2CH_2-$, or $-CH_2CH(CH_3)CH_2-$, or $-CH_2C(CH_3)_2CH_2-$;
$R_8$ is hydrogen or $C_1$ to $C_3$-alkyl;
$R_9$ is $C_1$ to $C_2$-alkyl;
$R_{60}$ is hydrogen or $C_1$ to $C_2$-alkyl;
r is 2, 3 or 4.

The products of these reactions can be isolated and purified by conventional means. In some of the formulas where wavy lines are used, the wavy line bond ($\sim$) between an oxygen atom and a carbon atom of the cycloalkyl ring can indicate either a solid-line bond(—) (up or above the plane of the ring) or a dashed line bond (- - -) (down or below the plane of the ring), and thus each of these formulas can represent a mixture of the two oxygen-group epimers or one or the other single epimer of unspecified stereochemistry.

In these Charts, $R_{10}$ is R or a suitable nitrogen protecting group; $R_{11}$ is $R_1$ or a suitable nitrogen protecting group; $R_{12}$ is $R_2$ or a suitable nitrogen protecting group; $R_7$ is hydrogen or a suitable nitrogen protecting group. Examples of suitable nitrogen protecting groups are:
(1) benzyl ($C_6H_5-CH_2-$);
(2) triphenylmethyl(trityl,$(C_6H_5)_3C-$);
(3) para-toluenesulfonyl (p—$CH_3-C_6H_4-SO_2-$); and
(4) trialkylsilyl, for example, trimethylsilyl (($CH_3)_3Si-$) or tertiary butyldimethylsilyl (($CH_3)_3CSi(CH_3)_2-$) and the like.

Introduction and removal of such nitrogen protecting groups are well known in the art of organic chemistry: See, for example,
(1) J. F. W. McOmie, Advances in Organic Chemistry, Vol. 3, pages 191-281 (1963);
(2) R. A. Boissonas, Advances in Organic Chemistry, Vol. 3, pgs. 159-190 (1963);
(3) "Protective Groups in Organic Chemistry", J. F. W. McOmie, ed., Plenum Press, New York, 1973, pg. 74.

The amines of the formulas $HNR_{10}R_7$ and $HNR_{11}R_{12}$ are either known in the art or are prepared by standard methods.

Under certain circumstances it is necessary to protect two different nitrogens with different protecting groups such that one such protecting group can be selectively removed while leaving the second protecting group in place. For example, the trityl and benzyl protecting groups can be used in this way, the trityl group being removable in the presence of the benzyl group under acidic conditions.

The requirements for protective groups in Charts A through I are generally well recognized by one skilled in the art of organic chemical synthesis, and the use, when required, of the appropriate protecting group or groups is indicated in these Charts by the use of the symbols $R_{10}$, $R_{11}$, $R_{12}$, and $R_7$; removal of a protecting group is implied when $R_{10}$, $R_{11}$, $R_{12}$ or $R_7$ is replaced in a subsequent formula by R, $R_1$, $R_2$, or H, respectively; N-protected compounds can be deprotected as desired by known methods.

Chart A outlines a preferred general procedure for preparing some cycloaliphatic diamine starting materials via a silyl-protected hydroxy group on a ring carbon atom adjacent to either of the ring carbon atoms which will bear the amido-nitrogen or the amino-nitrogen atoms.

The starting 2-cycloalken-1-ols are well known in the art. The process begins by oxidation of the desired, selected C$_5$ to C$_7$-2-cyclo-alken-1-ol (XI) with a suitable organic peracid such as m-chloroperbenzoic acid in a suitable organic solvent such as chloroform, preferably with cooling to 0° C. or lower, to produce the epoxy-cycloalkanol (XII), which is produced as a mixture of two epimers, exemplified by the wavy line chemical bond between the hydroxyl group and the cycloalkyl ring. If desired, known procedures can be used to separate the epoxy-cycloalkanol epimer having the epoxide and hydroxyl functions on the same side of the cycloaliphatic ring from the epimer having the epoxide and hydroxyl functions on opposite sides of the plane of the cycloaliphatic ring. In our work with this epoxidation-silylation sequence, the epimer (isomer) having the epoxide and hydroxyl on the same side of the cycloaliphatic ring has been observed to be the more abundant epimer in this intermediate product. The epoxycycloalkanol (XII) can be used in this process either as a mixture or after separating the epimers to obtain predominantly specific isomer intermediates.

Subjecting the epoxy-cycloalkanol compounds (XII) to suitable silylating conditions such as with tert-butyl-dimethyl-silylchloride, or an equivalent protecting group, in the presence of imidazole in dimethylformamide (DMF) at about 0° C. provides the silyloxy-epoxycycloalkane compound (XIII). Alternatively, one can also silylate the starting C$_5$ to C$_7$-2-cycloalken-1-ol, (XI), before epoxidation, as described above; the double bond of this silyated 2-cycloalken-1-ol compound (XIV) can then be epoxidized to produce the silyloxy-epoxy-cycloalkane (XIII) as a mixture of two epoxide epimers. In our work with this silylation-epoxidation sequence, the epimer with the epoxide and the silyl-protected hydroxyl functions on opposite sides of the plane of the cycloaliphatic ring has been observed to be the more abundant of the two product isomers. That is, by reversing the sequence of the reactions, the minor product isomer from the first described epoxidation-silylation sequence becomes the major product of the silylation-epoxidation sequence.

Reaction of the silyloxy-epoxy-cycloalkane (XIII) with a selected amine, HNR$_{11}$R$_{12}$, which amine can be used in excess to serve as both reactant and reaction medium, optionally in the presence of water, and at elevated temperature to promote reaction, opens the epoxide ring and places the amine on a carbon atom adjacent to the carbon atom bearing the resulting hydroxyl group to give the silyloxy-amino-alcohol compound (XVII). Alternatively, the silylated-epoxy compound can be reacted with the selected amine HNR$_{11}$R$_{12}$ in the presence of aluminum oxide in a suitable organic solvent such as diethyl ether at room temperature to obtain the silyloxyamino-alcohol (XVII) with methanesulfonyl chloride in the presence of a suitable acid scavenger such as triethylamine in a suitable organic solvent such as methylene chloride or chloroform, preferably with cooling to around 0° C. forms a resulting methanesulfonate ester intermediate. Then treatment of that methanesulfonate ester reaction mixture with an excess of an amine of the formula HNR$_{11}$R$_7$, optionally in the presence of water, which reaction replaces the methanesulfonyl ester group with an amine group, forms the silyloxy-cycloaliphatic diamine (XVIII).

Alternatively, here, the silyloxy-epoxy-cycloalkane (XIII) is reacted with an amine of the formula, HNR$_{10}$R$_7$, which may be used in excess to serve as both reactant and reaction medium, optionally in the presence of water at elevated temperatures, e.g., reflux temperature of the mixture, for a time sufficient to form the silyloxy-aminoalcohol (XV). Then, reaction of the silyloxy-amino-alcohol (XV) with methanesulfonyl chloride, as described above, to form the methanesulfonate ester, followed by reaction of that ester intermediate with the desired HNR$_{11}$R$_{12}$ amine gives a silyloxy-cycloaliphatic-diamine structure (XVI).

Chart B shows a preferred procedure for acylation-O-deprotection of the silyloxy-cycloaliphatic-diamines (XVI) and (XVIII) of Chart A. The hydroxyl group of the resulting hydroxy 2-amino benzamide or benzeneacetamide compounds can be oxidized to ketone as described hereinbelow.

The silyloxy-cycloaliphatic-diamines (XVI) and (XVIII) of Chart A can both be represented by the single generalized formula (XXI) of Chart B. The selected silyloxy-cycloaliphatic diamine compound (XXI) is reacted with a suitable acyl source, as indicated above, followed by treatment of the reaction mixture with a mineral acid in a suitable solvent such as ethanol to remove the silyl group to produce the desired-phenylacetamide or -benzamide alcohol (XXII).

In a procedure which is not a preferred one for producing ketals of this invention, the hydroxy amino amide (XXII) is oxidized with Jones reagent (chromic acid in sulfuric acid in water) in acetone solvent to produce the corresponding ketone, XXIIa, which is converted to a ketal by reaction as described herein.

Chart C outlines a preferred general procedure for preparing the adjacent ketal group-substituted cycloaliphatic trans diamine starting materials via the selected cycloaliphatic epoxy ketals. The cycloaliphatic trans diamine ketals so obtained can then be acylated with the desired acyl group, as described above, to form the desired trans-phenylacetamide or -benzamide having a ketal group on a cycloaliphatic ring carbon atom which is adjacent to a ring carbon atom bearing the amido-nitrogen or the amino-nitrogen.

The starting cycloaliphatic epoxy ketals, having the ketal group on the ring carbon atom adjacent to a cycloalkyl ring carbon atom bearing the epoxy function can be prepared by procedures known in the art, such as are described in *Journal of Medicinal Chemistry*, 1977, Vol. 20. No. 7, pp. 930–934, which described the preparation of the epoxy cyclohexane ketals, 7-oxabicyclo(4.1.0-)heptan-2-one ethylene ketal, therein, and which reference refers to *Journal of Organic Chemistry*, Vol. 30, No. 7, July 1965, pp. 2109–2120, which described a generalized procedure for preparing a variety of cycloalkenone ketals, and *Journal of Medicinal Chemistry*, 1972 Vol. 15, No. 2, pp. 171–177, which describes, inter alia, the preparation of an adjacent epoxy cyclopentane ketal, named 6-oxabicyclo[3.1.0]hexane-2-one ethylene ketal. The various ketals of this invention can be prepared by replacing ethylene glycol with 1,3-propylene glycol, 2-methyl-1,3-propylene glycol or 2,2-dimethyl-1,3-propylene glycol in the preparation.

The Chart C process begins by reacting the selected epoxy cycloalkanone ketal (XXXI) with the desired amine HNR$_{11}$R$_{12}$ as described above to produce the trans-2-amino-cycloalkanol ketal (XXXII), which cycloalkanol ketal is then reacted with methanesulfonyl chloride, as described above, to prepare the sulfonate ester intermediate, which ester is not usually isolated, and which ester is then reacted with an amine of the formula HNR$_{10}$R$_7$, as described above to produce transcycloalkanediamine ketal compound (XXXIII).

Alternatively, reaction of the starting epoxycycloalkane ketal (XXXI) with an amine of the Formula $HNR_{10}R_7$ as described above, produces trans-2-aminocycloalkanol ketal (XXXIV), which is then reacted with methanesulfonyl chloride by procedures described above to prepare the unisolated sulfonate ester, which is then reacted with the selected amine of the formula, $HNR_{11}R_{12}$, as described above, to produce the trans diamine ketal (XXXV).

The two trans diamine ketals (XXXIII) and (XXXV) can both be represented by the single generalized formula (XXXVI). This trans diamine ketal compound is reacted with the selected acyl source as described above to produce the trans amino-amide ketal (XXXVII).

Optionally, if it is desired to prepare the hydroxy-trans-amino-amide (XXXIX), one can react the trans-amino-amide ketal (XXXVII) with an aqueous mineral acid such as hydrochloric or sulfuric acid to produce the keto-trans-amino-amide (XXXVIII). The keto-trans-amino-amide (XXXVIII) can be used directly to prepare the compounds of this invention or it can then be reduced with a suitable reducing agent such as sodium borohydride in a suitable solvent such as ethanol at about 0° C. to 30° C. to produce the hydroxy-trans-amino-amide compound (XXXIX) which is obtained in two isomeric forms of which the more abundant is the isomer having the hydroxyl and the adjacent nitrogen group substituents on opposite sides of the plane of the cycloaliphatic ring.

Alternatively, reduction of the keto-trans-amino-amide compound (XXXVIII) with potassium tri-sec-butylborohydride (e.g., K-Selectride®) in a suitable organic solvent such as tetrahydrofuran, preferably at low temperature, e.g., $-10°$ C. to $+10°$ C., produces the hydroxy-trans-amino-amide (XXXIX) wherein the predominate or exclusive isomer form of the compound is one in which the hydroxyl function and the adjacent nitrogen group substituent are on the same side of the plane of the cycloaliphatic ring.

Of course, the hydroxy-trans-amino-amide compounds (XXXIX) can be used as intermediates to prepare thiol compounds of this invention.

The processes of Chart D are used in a preferred procedure to prepare cis amino amides wherein p of Formula I is zero. The starting α-chloro ketones of the formula (XLI) are well known in the art. An α-chloro ketone (XLI) is converted to the chloro enamine (XLII) by standard methods, for example, by the reaction with an amine of the formula, $HNR_{10}R_7$, in the presence of anhydrous magnesium sulfate in a suitable solvent such as benzene or toluene. This chloro enamine (XLII) is reacted with the sodium salt of benzyl alcohol in benzyl alcohol solvent, according to D. Cantacuzene, et al., Tetrahedron Letters, pp. 4807–4810 (1971), to give a benzyoxy enamine (XLIII). This enamine (XLIII) is reacted with a chloroformate of the formula, Cl—$CO_2R_9$, or an acid anhydride of the formula, $(R_9O)_2$-C=O in a suitable inert solvent such as tetrahydrofuran to provide an enamine (XLIV). Hydrogenation of this enamine (XLIV) over a platinum catalyst in a suitable solvent such as ethyl acetate yields a mixture of alcohol epimers of a cis amino ester (XLV). Benzylation of the hydroxyl of a formula (XLV) alcohol gives benzyl ether (XLVI) and subsequent Curtius reaction, that is, for example, reaction with hydrazine to form an acyl hydrazide, which is reacted with nitrous acid to produce an acyl azide, which undergoes Curtius rearrangement to afford after acidification with aqueous hydrogen chloride epimeric benzyloxy cis diamines (XLVII). Conversion of a formula (XLVII) diamine to a hydroxy cis amino amide (XLVIII) is then achieved by introducing the desired $R_1$ and $R_2$ groups (if other than hydrogen) by standard alkylation procedures, manipulating the N-protecting groups to allow acylation of the nitrogen on the ring carbon adjacent to the ring carbon bearing the oxygen substituent as indicated in Chart D, and finally deprotecting. Alternatively, with the proper manipulation of protecting groups using methods described above, the hydroxyl group is oxidized to provide the corresponding ketone which can be converted to a desired ketal of this invention by reaction with the appropriate trialkylorthoformate and alkanol as described herein.

The process of Chart E are somewhat analogous to those of Chart D and are used in a preferred procedure to prepare cis amino amides (LVIII) of an α-chloro ketone (LI) is reacted with an amine of the formula, $HNR_{11}R_{12}$, as described for Chart D to provide an enamine (LII). This enamine (LII) is converted to a benzyloxy cis diamine (LVII) (as a mixture of benzyloxy epimers) as described for the analogous transformation in Chart D. A benzyloxy cis diamine (LVII) is converted to a hydroxy cis amino amide (LVIII) by alkylation of the primary nitrogen by standard methods, acylation of the same nitrogen as shown in Chart E and (if necessary) deprotection. The hydroxyl function of a formula (LVIII) hydroxy cis amino amide is reacted to produce the desired ketone compound as described above for a formula (XLVIII) compound of Chart D.

The processes of Chart F are used to prepare cis amino amide ketals (LXVII) wherein p of Formula I is zero. As described above, the starting ketal epoxides of the formula (LXI) are known in the art or can be prepared by methods known in the art. A ketal epoxide (LXI) is reacted with an amine of the formula, $HNR_{11}R_{12}$, by a method described above, to afford a trans amino alcohol (LXII). The hydroxyl of an amino alcohol (LXII) is oxidized with Jones reagent, as described above, in acetone to give an amino ketone (LXIII), which is reacted with an amine of the formula, $H_2NR_{10}$, to give an imine (LXIV). Reduction of imine (LXIV) with a suitable reducing agent such as lithium aluminum hydride or sodium cyanoborohydride produces a mixture of cis and trans diamino ketals of the formulas (LXV) and (LXVI), respectively, which mixture can be separated or reacted in the next step. A cis diamino ketal (LXV) (or a cis-trans mixture of diamines (LXV) and (LXVI) from the reduction step) is reacted with a suitable acyl source as described above to provide after purification a cis amino amide ketal (LXVII). A cis amino ketal (LXVII) is reacted with mineral acid as described above to generate a cis amino amide ketone of the formula (LXVIIa), which can be reduced to the epimeric alcohols by reduction with a suitable reducing agent as described above.

The processes of Chart G are somewhat analogous to those of Chart F and using methods described above are used to prepare cis amino amide ketals (LXXVIII) and ketones (LXXVII) wherein n of Formula I is zero. A ketal epoxide (LXXI) is reacted with an amine of the formula $HNR_{10}R_7$ to afford a trans amino alcohol (LXXII), which is oxidized, e.g., with Jones Reagent as defined above, to an amino ketone (LXXIII). An amino ketone (LXXIII) is reacted with an amine of the formula $H_2NR_8$ to provide an imine (LXXIV), which is reduced to yield a mixture of cis and trans diamino ketals of the formulas (LXXV) and (LXXVI). A cis diamino ketal (LXXV) (or a cis-trans mixture (LXXV) and (LXXVI) from the reduction step) is alkylated by standard methods to introduce the desired $R_{11}$ and $R_{12}$ substituents to afford cis amino ketal (LXXVII), which is reacted with a suitable acyl source as described above to yield after purification a cis amino amide ketal (LXXVIII). A cis amino amide ketal (LXXVIII) is reacted with mineral acid as described above to give a cis amino amide ketone of the formula LXXVIIIa which can be reduced to the epimeric alcohols by reduction with a suitable reducing agent as described above.

The processes of Chart H are used to prepare cis amino amide alcohols (LXXXVIII) and ketones (LXXXVIIIa), wherein p of Formula I is zero. The starting allylic bromides of the formula (LXXXI) are well known in the art. An allylic bromide (LXXXI) is reacted with an amine of the formula $HNR_{11}R_{12}$, in the presence of triethylamine, to afford an amino olefin of the formula (LXXXII), which is epoxidized to give after purification an epoxide (LXXXIII). An epoxide (LXXXIII) is reacted with an amine of the formula $H_2NR_{10}$ to give a diamino alcohol (LXXXIV), which is reacted with chlorosulfonic acid. The resulting sulfate ester is reacted with sodium hydroxide to give an amino aziridine (LXXXV). Alternatively an arizidine (LXXXV) is obtained from the amino olefin (LXXXII) by a method described by F. Fieser and L. Fieser, *Reagents for Organic Synthesis*, Volume 2, Wiley-Interscience, New York, N.Y., 1969, page 223. Reaction of an amino olefin (LXXXII) with iodine isocyanate produces a trans iodo isocyanate which is converted to a carbamate by reaction with methanol. This carbamate is reacted with potassium hydroxide in methanol to produce, after purification, an aziridine which can be alkylated, if necessary, to give an aziridine of the formula (LXXXV). Heating an aziridine (LXXXV) with a carboxylic acid of the formula $R_6CO_2H$ gives a diamino ester (LXXXVI). Acylation of a diamino ester (LXXXVI) with a suitable acyl source as described above yields a cis amino amide ester (LXXXVII). Saponification of the ester group of a formula (LXXXVII) ester by standard methods affords a cis amino amide alcohol (LXXXVIII). Using methods described above, an alcohol (LXXXVIII) is oxidized with Jones reagent in acetone to provide a ketone of the formula (LXXXVIIIa). Using methods described above, this resulting ketone is converted to a desired ketal or this ketone is reduced to give the alcohol epimer with stereochemistry substantially opposite to that of the formula (LXXXVIII) alcohol.

The processes of Chart I are somewhat analogous to those of Chart H and are used to prepare cis amino amide alcohols of the formula (XCIX) and ketones (XCIXa), wherein n of formula I is zero. An allylic bromide (XCI) is reacted with an amine of the formula $HNR_{10}R_7$, in the presence of triethylamine, to give an amino olefin (XCII), which is epoxidized to give after purification an epoxide (XCIII). An epoxide (XCIII) is reacted with an amine of the formula $H_2NR_8$ to give a diamine alcohol (XCIV), which is reacted with chlorosulfuric acid. The resulting sulfate ester is reacted with sodium hydroxide to give an amino aziridine (XCV). Alternatively an amino olefin (XCII) is converted to an aziridine (XCV) by the iodine isocyanate method described above. Heating an aziridine (XCV) with a carboxylic acid of the formula $R_6CO_2H$ gives a cis diamino ester (XCVI). Alkylation of the nitrogen on a ring carbon atom adjacent to the ring carbon atom bearing the oxygen substituent by standard methods gives a cis diamino ester (XCVII). Acylation of a cis diamino ester (XCVII) with a suitable acyl source as described above yields a cis amino amide ester (XCVIII) of this invention. Saponification of the ester group of a formula (XCVIII) ester by standard methods yields a cis amino amide alcohol (XCIX). Using methods described above, an alcohol (XCIX) is oxidized with Jones Reagent in acetone to provide a ketone of the formula (XCIXa). Using methods described above, this resulting ketone is converted to a desired ketal or this ketone is reduced to give the alcohol epimer with stereochemistry substantialy opposite to that of the formula (XCIX) alcohol.

In addition to the above described procedures, one can also form the di—$C_1$ to $C_2$-alkyl ketal derivative of the compound XXXI (Chart C), LXI (Chart F), LXXI (Chart G), by replacing the glycol with the trialkylorthoformate and corresponding alkanol as described hereinabove to form the selected epoxy dialkyl ketal derivative of compounds XXXI, LXI, or LXXI, respectively, which derivatives can be carried through that Chart C, F, or G process, respectively, to desired adjacently dialkyloxy-substituted amino-amides, analogous to structures XXXVII, LXVII, or LXXVIII, respectively.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active limitations inherent in the art of compounding such an essential active material for beneficial effects in humans and animals as ,isclosed in detail in this specification under preferred embodiments, those being features of the present invention Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcuim carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that any syringeability exsists. Such preparations must be stable under the conditions of manufacture and storage, and ordinarily contain, in addition to the principal solvent or supending liquid, preservatives in the nature of bacteriostatic and fungistatic agents, for example, parabens, chlorobutanol, benzyl, alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparation for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg per kg to about 5 mg per kg of body weight of the recipient.

Preferred dosages for most applications are 0.05 to 2.0 mg per kg of body weight.

The useful pharmaceutical dosage unit forms of these compounds in pharmaceutical formulations is preferably adapted for systemic administration to obtain analgesic effects comprising an effective, non-toxic amount of a compound according to Formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compound in various pharmacological test procedures which measure analgesia and the physical dependence liability of the test compounds in standard laboratory test animals.

This invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, $CH_2Cl_2$ means methylene chloride solvent, $K_2CO_3$, $MgSO_4$, or $Na_2SO_4$ means the organic layer was dried over anhydrous forms of these salts, mp means melting point, NMR means a nuclear magnetic resonance spectrum, and DBN means 1,5-diazabicyclo[4.3.0]non-5-ene; h means hour(s), $N_2$ means nitrogen, tlc means thin layer chromatography procedures, $Na_2SO_3$ means sodium sulfite, $NaHCO_3$ means sodium bicarbonate, DMSO is dimethylsulfoxide, SKellysolve B (or Skelly B) is a tradename for a solvent of essentially n-hexane, bp 60°-68° C. (Merck Index, Ninth Edition ((1976) page 1106), $Et_2O$ means diethyl ether, MeOH means methanol, THF means tetrahydrofuran, $H_2O$ means water, $CHCl_3$ means chloroform, brine is saturate aqueous sodium chloride solution, DMF means N,N-dimethylformamide, $Et_3N$ is triethylamine, HRMS means high resolution mass spectrum, EtOAc means ethyl acetate, GC (or g.c.) means gas chromatography, GLPC means gas liquid phase chromatography.

EXAMPLE 1

($\pm$)-(1$\alpha$,2$\beta$)-4-bromo-N-methyl-N-[3,3-dimethoxy-2-(1-pyrrolidinyl)cyclohexyl]benzamide

A.

trans-($\pm$)-1-[7-methylamino)-1,4-dioxaspiro[4.5]dec-6-yl]-pyrrolidine, monohydrochloride A solution of 38.9 g (0.249 mole) of spiro[1,3-dioxolane-2,2'-[7]-oxabicyclo[4.1.0]heptane][1] in 50 ml pyrrolidine and 2 ml $H_2O$ was heated to 86° for eighteen hours. The excess pyrrolidine was removed via rotovap and the residue distributed between EtOAc and $H_2O$. The phases were separated and the organic phase washed with $H_2O$, dried ($MgSO_4$) and concentrated in vacuo leaving 31 g of crude oil. The oil was chromatographed on 1500 g of RP-2 silica gen eluting with EtOAc to give 26.5 g (47%) of the trans amino alcohol, trans -($\pm$)-7-(1-pyrrolidinyl)-1,4-dioxaspiro[4.5]decan-6-ol.
[1]The starting material was prepared according to the procedure by R. Vince et al. *J. Med. Chem.*, 20, 930 (1977).

A solution of 26.5 g (0.117 mole) of the trans amino alcohol in 300 ml $CH_2Cl_2$ and 17.76 g (0.175 mole) of $Et_3N$ was cooled in an ice bath under $N_2$. To this solution was added over a thirty minute period 20.1 g (0.175 mole) of methanesulfonyl chloride and the reaction was stirred for two hours. The mixture was distributed between $CH_2Cl_2$ and $H_2O$, the phases separated, the organic phase dried ($MgSO_4$) and concentrated in vacuo. The residue was placed in a stainless steel bomb with 200 ml of methylamine and heated on a steam bath for two days. The bomb was cooled, vented and the excess methylamine evaporated. The residue was distributed between EtOAc and $H_2O$ and the organic phase separated, washed with $H_2O$, brine, dried ($MgSO_4$) and concentrated in vacuo. The crude oil was chromatographed on 500 g of RP-2 silica gel eluting with EtOAc then MeOH-$NH_4OH$-EtOAc, 1.8:0.2:98 (v:v) to give 14.65 g (50% from the amino alcohol) of the subtitled trans diamine. NMR ($CHCl_3$): $\delta$0.8–1.9 (m,10H, ring $CH_2$—), 1.9–2.3 (m, 1H, CH–NH). 2/45 (s, 3H, $CH_3$—N), 2.5–3.2 (m, 5H, $CH_2$—N, 3.75–4.2 (m, 4H, $CH_2O$).

B.

trans-($\pm$)-4-Bromo-N-methyl-N-[6-(1-pyrrolidinyl)-1,4-dioxaspiro[4.5]dec-7-yl]benzamide, monohydrochloride To a stirred solution of 7.2 g (0.03 mole) of trans-($\pm$)-1-[7-(methylamino)-1,4-dioxaspiro[4.5]dec-6-yl]pyrrolidine in 200 ml $Et_2O$ and 3.64 g (0.036 mole) of triethylamine was added a solution of 7.9 g (0.036 mole) of 4-bromobenzoyl chloride in 50 ml $Et_2O$ over thirty minutes under $N_2$. After two hours the slurry was filtered and the salt washed with $Et_2O$. The combined ethereal layers were washed with H₂O, 10% NaOH, H₂O, brine, dried (MgSO₄) and concentrated in vacuo. The residue was treated with Et₂O/HCl and the resultant precipitate recrystallized from MeOH/EtOAc to give 7.0 g, mp 218°–219° and 1.68 g, mp 212°–214° (56%) of the titled amide: mp 219–220.5. The nmr and ir spectra were in accord with the titled amino amide ketal.

Anal. Calcd. for $C_{20}H_{28}BrClN_2O_3$: C, 52.24; H, 6.14; Br, 17.38; Cl, 7.71; N, 6.09. Found: C. 51.88, H, 6.24; Br, 17.36; Cl, 7.78; N, 6.40.

C.
trans-(±)-4-Bromo-N-methyl-N-[3-oxo-2-(1-pyrrolidinyl)cyclohexyl]benzamide, monohydrobromide To 12 ml of concentrated $H_2SO_4$ in a glass beaker was added 2.2 g (0.0048) of the amino amide ketal prepared as described in Example 1B. The mixture was stirred until the solid had dissolved and the foaming had ceased. The solution was quickly diluted with ice and made basic (pH 14) with 50% NaOH while maintaining ice bath temperatures. The product was extracted with EtOAc and the extract washed with H₂O, dried (MgSO₄) and concentrated in vacuo. Although the free base was a crystalline compound (mp 145-149), it was unstable as indicated by the broadening of the melting point upon subsequent recrystallizations. Therefore, the hydrobromide salt was made with Et₂O/-HBr and the resultant precipitate recrystallized from MeOH-EtOAc to give 0.29 g (16%) of the titled compound: mp 190°–196° C. The ir and nmr spectra were in accord with the titled compound.

Anal. Calcd. for $C_{18}H_{24}Br_2N_2O_2$: C, 46.98; H, 5.26; Br, 34.73; N, 6.09. Found: C, 47.08; H, 5.27; Br, 34.20; N, 5.99.

D.
(±)-(1α,2β)-4-Bromo-N-methyl-N-[3,3-dimethoxy-2-(1-pyrrolidinyl)cyclohexyl]benzamide, and its hydrochloride To a solution of 1.0 g of trans-(±)-4-bromo-N-methyl-N-[3-oxo-2-(1-pyrrolidinyl)cyclohexyl]benzamide, prepared as described in Example 1C above, in fifty ml of dry methanol there is added 5 ml of trimethylorthoformate and 0.5 ml of 4M methanolic hydrogen chloride. The resulting mixture is refluxed for about 16 hours, cooled, and the solvent is removed in vacuo. The residual oil is crystallized from a hot methanol solution thereof diluted with diethyl ether until the mixture becomes cloudy to obtain the titled 4-bromo-N-methyl-N-[3,3-dimethoxy)-2-(1-pyrrolidinyl)cyclohexyl]benzamide, which is converted to a hydrochloride salt.

EXAMPLE 2
(±)-(1α,2β)-3,4-Dichloro-N-methyl-N-[3,3-diethoxy-2-(1-pyrrolidinyl)cyclohexyl]benzeneacetamide, as a hydrochloride salt Following the procedure of Example 1, but substituting (±)-(1α,2β)-3,4-dichloro-N-methyl-N-[3-oxo-2-(1-pyrrolidinyl)cyclohexyl]benzeneacetamide for the (±)-4-bromo-N-methyl-N-[3-oxo-2-(1-pyrrolidinyl)-cyclohexyl]benzamide and triethylorthoformate for the trimethylorthoformate in 50 ml of dry ethanol instead of methanol, there is obtained as product (±)-(1α,2β)-3,4-dichloro-N-methyl-N-[3,3-diethoxy-2-(1-pyrrolidinyl)-cyclohexyl]benzeneacetamide, as a hydrochloride salt.

EXAMPLE 3
Trans-(±)-3,4-dichloro-N-methyl-N-[6,6-dimethoxy-2-(1-pyrrolidinyl)cyclohexyl]benzeneacetamide

A.
Trans-(±)-3,4-dichloro-N-methyl-N-[7-(1-pyrrolidinyl)-1,4-dioxaspiro[4.5]dec-6-yl]benzeneacetamide To a stirred solution of 0.03 mole of trans-(±)-1-[6-methylamino-1,4-dioxaspiro[4.5]dec-7-yl]pyrrolidine in 200 ml of diethyl ether and 0.036 mole of triethylamine, there is added a solution of 0.036 mole of 3,4-dichlorophenylacetyl chloride in 300 ml of diethyl ether over 30 minutes under nitrogen. After two hours the mixture is filtered and the solid washed with diethyl ether. The combined ethereal layers were washed with water, 10% sodium hydroxide in water solution, water, brine, dried over magnesium sulfate and concentrated in vacuo. The residue is treated with a diethyl ether solution of hydrogen chloride and the resultant precipitate is recrystalized from a methanol/ethyl acetate mixture to give trans-(±)-3,4-dichloro-N-methyl-N-[7-(1-pyrrolidinyl)-1,4-dioxaspiro[4.5]-dec-6-yl]benzeneacetamide, monohydrochloride.

B.
Trans-(±)-3,4-dichloro-N-methyl-N-[6-oxo-2-(1-pyrrolidinyl)cyclohexyl]benzeneacetamide, and its hydrobromide To 12 ml of concentrated sulfuric acid solution in a glass beaker, there is added 0.0048 mole of the trans-(±)-3,4-dichloro-N-methyl-N-[7-(1-pyrrolidinyl)1,4-dioxaspiro[4.5]dec-6-yl]benzeneacetamide, prepared as described in Part A, hereinabove. The mixture is stirred unitl the solid has dissolved and any foaming has ceased. The solution is quickly diluted with ice and made basic (pH 14) with 50% sodium hydroxide in water solution while maintaining ice bath temperature. The product is extracted with ethyl acetate and the extract is washed with water, dried over magnesium sulfate and concentrated in vacuo. The hydrogen bromide salt of the free base product is made by treating the base product with hydrogen bromide in diethyl ether. The titled 6-oxo-benzeneacetamide intermediate compound is recrystallized from a methanol/ethyl acetate mixture.

C.
trans-(±)-3,4-dichloro-N-methyl-N-[6,6-dimethoxy-2-(1-pyrrolidinyl)cyclohexyl]benzeneacetamide and its hydrochloride To a solution of trans-(±)-3,4-dichloro-N-methyl-N-[6-oxo-2-(1-pyrrolidinyl)cyclohexyl]benzeneacetamide, prepared as described in Part B hereinabove, in 50 ml of dry methanol there is added 5 ml of trimethylorthoformate and 0.5 ml of 4M methanolic hydrogen chloride. The resulting mixture is refluxed for about 16 hours, cooled, and the solvent is removed in vacuo. The residual oil is crystallized from a hot methanol solution thereof, diluted with diethyl ether until the mixture becomes cloudy to obtain the titled trans-(±)-3,4-dichloro-N-methyl-N-[6,6-dimethoxy-2-(1-pyrrolidinyl)cyclohexyl]benzeneacetamide, which is converted to a hydrochloride salt.

EXAMPLE 4

Trans-(±)-3,4-difluoro-N-methyl-N-[2-(1-azetidinyl)-6,6-diethoxycyclohexyl]benzeneacetamide and its hydrochloride salt Following the procedure of Example 3, substituting trans-(±)-3,4-difluoro-N-methyl-N-[6-oxo-2-(1-azetidinyl)cyclohexyl]benzeneacetamide for the trans-(±)-3,4-dichloro-N-methyl-N-[6-oxo-2-(1-pyrrolidinyl)cyclohexyl]benzeneacetamide in 50 ml of dry ethanol instead of methanol and 5.0 ml of triethylorthoformate instead of trimethylorthoformate, there is formed as product trans-(±)-3,4-difluoro-N-methyl-N-[6,6-diethoxy-2-(1-azetidinyl)cyclohexyl]benzeneacetamide, which is converted to a hydrochloride salt.

Following the procedure of Examples 1, 2 and 3 above, and using as the starting ketone the appropriate 3-oxocycloalkylbenzeneacetamide of -benzamide starting material, there are prepared the cis and trans isomers of the following representative compounds within the scope of this invention:

a. 4-Trifluoromethyl-N-[3,3-dimethoxy-2-(1-pyrrolidinyl)cyclohexyl]-N-methylbenzeneacetamide,
b. 3-Trifluoromethyl-N-[3,3-diethoxy-2-(1-pyrrolidinyl)cyclohexyl]-N-methylbenzeneacetamide,
c. 4-Chloro-N-[3,3-dimethoxy-2-(1-azetidinyl)cyclohexyl]-N-methylbenzamide,
d. 4-Fluoro-N-[3,3-diethoxy-2-(1-piperidinyl)cycloheptyl]-N-ethylbenzeneacetamide,
e. 4-Nitro-N-[3,3-dimethoxy-2-(1-pyrrolidinyl)cycloheptyl]-N-(n-propyl)benzamide,
f. 4-Amino-N-[3,3-dimethoxy-2-(1azetidinyl)cyclopentyl]-N-methylbenzeneacetamide,
g. 3-Hydroxy-4-methyl-N-[3,3-dimethoxy-2-(1-pyrrolidinyl)-cyclohexyl]-N-methylbenzeneacetamide,
4-Azido-N-[3,3-diethoxy-2-(dimethylamino)cyclopentyl]-N-methylbenzamide,
i. 4-Cyano-N-[3,3-dimethoxy-2-(diethylamino)cyclohexyl]-N-methylbenzeneacetamide,
j. 4-Methanesulfonyl-N-[3,3-dimethoxy-2-(1-piperidinyl)cyclohexyl]-N-methylbenzamide,
k. 4-Methoxycarbonyl-N-[3,3-diethoxy-2-dimethylamino)cycloheptyl]-N-methylbenzeneacetamide,
l. 4-Acetyloxy-N-[3,3dimethoxy-2-(1-pyrrolidinyl)cyclohexyl]-N-methylbenzeneacetamide,
m. 4-Acetylamino-N-[3,3-diethoxy-2-(1-azetidinyl)cyclohexyl]-N-ethylbenzeneacetamide,
n. 4-Methoxy-3-chloro-N-[3,3-dimethoxy-2-(diallylamino)cyclohexyl]-N-methylbenzeneacetamide,
o. 4-Phenyl-N-[3,3-diethoxy-2-aminocyclohexyl]N-methylbenzamide,
p. 3,4-Dichloro-N-[3,3-dimethoxy-2-(1-pyrrolidinyl)cyclohexyl]-benzeneacetamide,
q. 4-Bromo-N-[3,3-diethoxy-2-(1-azetidinyl)cycloheptyl]benzamide,
r. N-[3,3-bis(methylthio)-2-(1-pyrrolidinyl)cyclopentyl]-3,4-dichloro-N-methylbenzeneacetamide,
s. N-[3,3-bis(methylthio)-2-(1-pyrrolidinyl)cyclopentyl]-4-bromo-N-methylbenzamide,
t. N-[3,3-bis(methylthio)-2-(1-pyrrolidinyl)cyclohexyl]-3,4-dichloro-N-methylbenzeneacetamide,
u. N-[3,3-bis(methylthio)-2-(1-pyrrolidinyl)cyclohexyl]-4-bromo-N-methylbenzamide,
v. N-[3,3-bis(ethylthio)-2-(1-pyrrolidinyl)cyclohexyl]-3,4-dichloro-N-methylbenzeneacetamide,
w. N-[3,3-bis(methylthio)-2-(1-pyrrolidinyl)cyclohexyl]-3,4-dichloro-N-methylbenzeneethanethioamide,
x. N-[3,3-bis(methylthio)-2-(1-pyrrolidinyl)cycloheptyl]-3,4-dichloro-N-methylbenzeneacetamide,
y. N-[3,3-bis(ethylthio)-2-(1-pyrrolidinyl)cycloheptyl]-4-bromo-N-methylbenzamide,
z. N-[3,3-bis(methylthio)-2-(methylamino)cycloheptyl]-3,4-dichloro-N-methylbenzeneacetamide,
aa. 3,4-dichloro-N-[3,3-dimethoxy-2-(1-pyrrolidinyl)cyclohexyl]-N-methylbenzeneethanethioamide,
bb. 4-bromo-N-[3,3-dimethoxy-2-(1-pyrrolidinyl)cyclohexyl]-N-methylbenzenecarbothioamide,
cc. 3,4-dichloro-N-[3,3-diethoxy-2-(1-pyrrolidinyl)cyclohexyl]-N-methylbenzeneethanethioamide,
dd. 4-bromo-N-[3,3-diethoxy-2-(1-pyrrolidinyl)cyclohexyl]-N-methylbenzenecarbothioamide,
ee. 3,4-dichloro-N-[3,3-dimethoxy-2-(1pyrrolidinyl)cycloheptyl]-N-ethylbenzeneethanethioamide,
ff. 4-bromo-N-[3,3-diethoxy-2-(1-pyrrolidinyl)cycloheptyl]-N-(1-propyl)benzenecarbothioamide,
gg. 3,4-dichloro-N-[3,3-dimethoxy-2-(1-pyrrolidinyl)cyclopentyl]-N-methylbenzeneethanethioamide,
hh. 4-bromo-N-[3,3-dimethoxy-2-(1-pyrrolidinyl)cyclopentyl]-N-methylbenzenecarbothiomide,
ii. 3-chloro-N-[3,3-dimethoxy-2-(1-piperidinyl)cyclohexyl]-N-ethylbenzeneethanethioamide,
jj. N-[3,3-diethoxy-2-(1-azetidinyl)cycloheptyl]-4-methylbenzeneethanethioamide,
kk. N-[3,3-diethoxy-2-[1-(dimethylamino)cycloheptyl]]-N-(1-propyl)-4-(trifluoromethyl)benzenecarbothioamide,
ll. N-[3,3-bis(methylthio)-2-[1-(diethylamino)cycloheptyl]]-N-methylbenzeneethanethioamide,
mm. 3-azido-N-[3,3-bis(ethylthio)-2-aminocyclohexyl]-N-(1-propyl)benzamide,
nn. N-[3,3-bis(methylthio)-2-(1-azetidinyl)cyclohexyl]-N-methyl-[1,1'-biphenyl]-4-ethanethioamide,
oo. N-[3,3-bis(ethylthio)-2-(1-piperidinyl)cyclopentyl]-4-(methanesulfonyl)-N-(1-methylethyl)benzamide,
pp. N-[3,3-bis(ethylthio)-2-(ethylmethylamino)cycloheptyl]-2-cyano-N-ethylbenzeneacetamide,
qq. 4-amino-N-[3,3-bis(methylthio)-2-(methylpropylamino)cycloheptyl]-N-methylbenzenecarbothioamide, Following the procedures of Examples 1, 2 and 3 above and using as the starting ketone the appropriate 5-oxocyclopentylbenzeneacetamide or -benzamide, 6-oxocyclohexylbenzeneacetamide or -benzamide, or 7-oxocycloheptylbenzeneacetamide or -benzamide starting material, there are prepared, respectively, the corresponding 5,5-derivatives for cyclopentyl compounds, the corresponding 6,6-derivatives for cyclohexyl compounds and the corresponding 7,7-derivatives for cycloheptyl compounds named in the above compound list.

Using the appropriate 3-hydroxycycloalkylbenzeneacetamide or -benzamide starting material, the following representative mercapto compounds of this invention are prepared by converting to a paratoluenesulfonate derivative, which is reacted with hydrogen sulfide:

rr. 3,4-dichloro-N-[3-mercapto-2-(1-pyrrolidinyl)cyclopentyl]-N-methylbenzeneacetamide,
ss. 4-bromo-N-[3-mercapto-2-(1-pyrrolidinyl)cyclopentyl]-N-methylbenzamide,
tt. 3,4-dichloro-N-[3-mercapto-2-(1-pyrrolidinyl)cyclohexyl]-N-methylbenzeneacetamide,
uu. 4-bromo-N-[3-mercapto-2-(1-pyrrolidinyl)cyclohexyl]-N-methylbenzamide, vv. 3-dichloro-N-[3-mercapto-2-(1-pyrrlidinyl)cyclohexyl]-N-methylbenzeneacetamide,
ww. 4-bromo-N-[3-mercapto-2-(1-azetidinyl)cyclohexyl]-N-methylbenzamide,
xx. 3,4-dichloro-N-[3-mercapto-2-(1pyrrolidinyl)cycloheptyl]-N-methylbenzeneacetamide,
yy. 4-bromo-N-[3-mercapto-2-(1-pyrrolidinyl)cycloheptyl]-N-methylbenzamide,
zz. N-[3-mercapto-2-(diallylamino)cyclopentyl]-N-ethyl-4-nitrobenzamide,
aaa. 3-methoxy-N-methyl-N-[3-mercapto-2-(1-pyrrolidinyl)-cyclopentyl]benzeneacetamide,
bbb. 3-hydroxy-N-methyl-N-[3-mercapto-2-aminocycloheptyl]benzeneacetamide.

Using as the starting alcohol the appropriate 5-hydroxycyclopentylbenzeneacetamide or -benzamide, 6-hydroxycyclohexylbenzeneacetamide or -benzamide, or 7-hydroxycycloheptylbenzeneacetamide or -benzamide starting material, there are prepared by converting to a para-toluenesulfonate derivative, which is reacted with hydrogen sulfide, respectively, the 5-mercaptocyclopentyl, 6-mercaptocyclohexyl, and 7-mercaptocycloheptyl compounds corresponding to the 3-mercapto compounds named above.

Using the appropriate 3-mercaptocycloalkylbenzeneacetamide or -benzamide starting material as listed above, the following representative 3-(alkylthio)cycloalkylbenzeneacetamide or -benzamide compounds of this invention are prepared by reaction with the corresponding alkyl halide:

ccc. 3,4-dichloro-N-[3-methylthio-2-(1-pyrrolidinyl)cyclopentyl]-N-methylbenzeneacetamide,
ddd. 4-bromo-N-[3-methylthio-2-(1-pyrrolidinyl)cyclopentyl]-N-methylbenzamide,
eee. 3,4-dichloro-N-[3-methylthio-2-(1-pyrrolidinyl)cyclohexyl]-N-methylbenzeneacetamide,
fff. 4-bromo-N-[3-methylthio-2-(1-pyrrolidinyl)cyclohexyl]-N-methylbenzamide,
ggg. 3,4-dichloro-N-[3-ethylthio-2-(1-pyrrolidinyl)cyclohexyl]-N-methylbenzeneacetamide,
hhh. 4-bromo-N-[3-(1-propylthio)-2-(1-pyrrolidinyl)cyclohexyl]-N-methylbenzamide,
iii. 3,4-dichloro-N-[3-methylthio-2-(1-pyrrolidinyl)cycloheptyl]-N-methylbenzeneacetamide,
jjj. 4-bromo-N-[3-methylthio-2-(1-pyrrolidinyl)cycloheptyl]-N-methylbenzamide,
kkk. N-[3-(ethylthio)-2-(diallylamino)cyclopentyl]-N-ethyl-4-nitrobenzamide,
lll. 3-methoxy-N-methyl-N-[3-(methylthio)-2-(1-pyrrolidinyl)cyclopentyl]benzeneacetamide,
mmm. 3-hydroxy-N-methyl-N-[3-(1-propylthio)-2-aminocycloheptyl]-benzeneacetamide.

Using as the starting material the appropriate 5-mercaptocyclopentylbenzeneacetamide or -benzamide, 6-mercaptocyclohexylbenzeneacetamide or -benzamide, or 7-mercaptocycloheptylbenzeneacetamide or -benzamide starting material, there are prepared by reaction with the corresponding alkyl halide, respectively, the 5-(alkylthio)cyclopentyl, 6-(alkylthio)cyclohexyl, or 7-(alkylthio)-cycloheptyl compounds corresponding to the 3-alkylthio compounds named above.

GENERAL CHEMICAL STRUCTURES

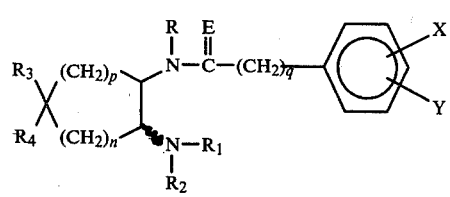

I

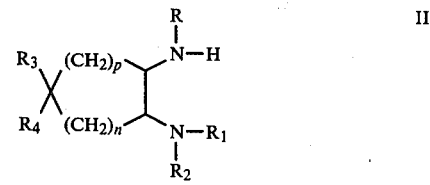

II

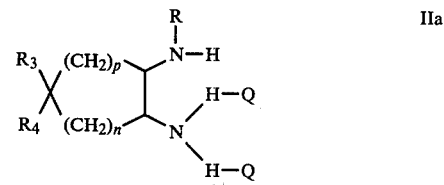

IIa

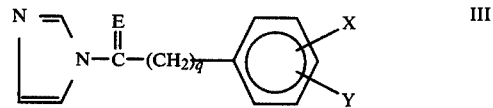

III

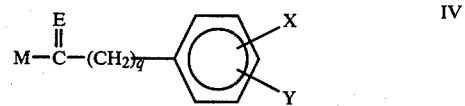

IV

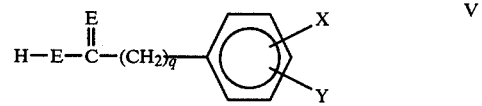

V

CHART A

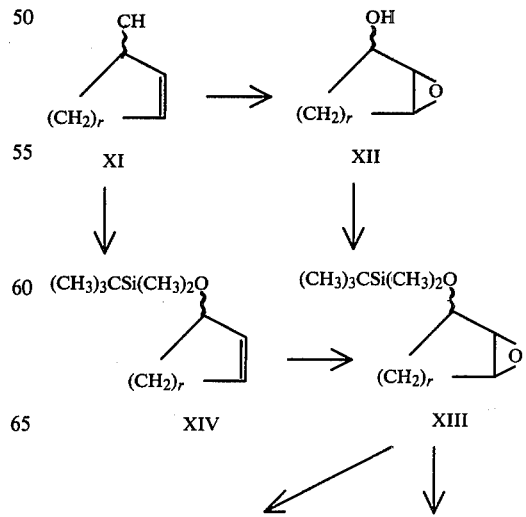

-continued
CHART A
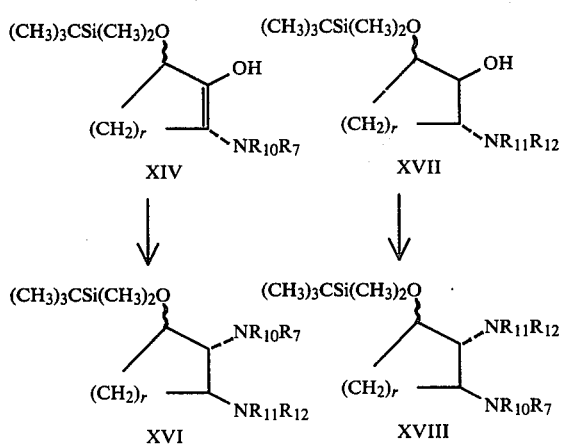
CHART B
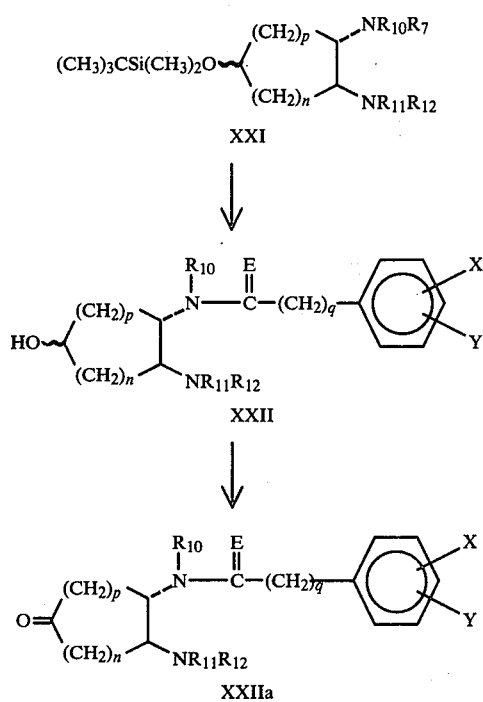
CHART C
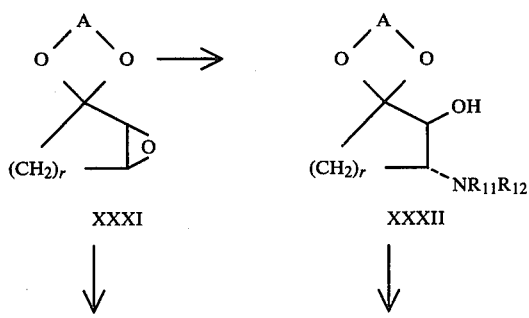
-continued
CHART C
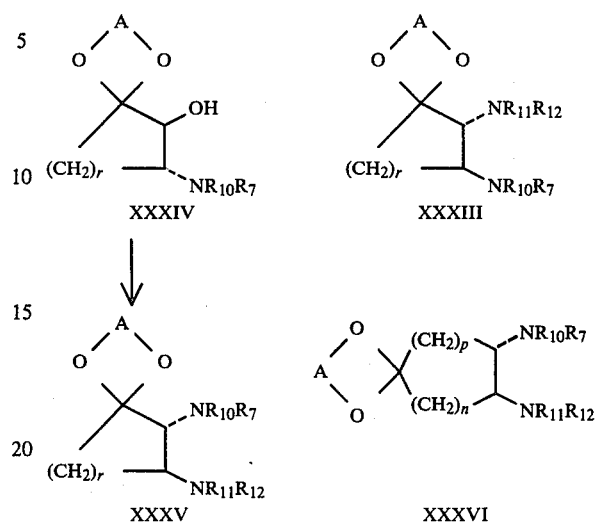
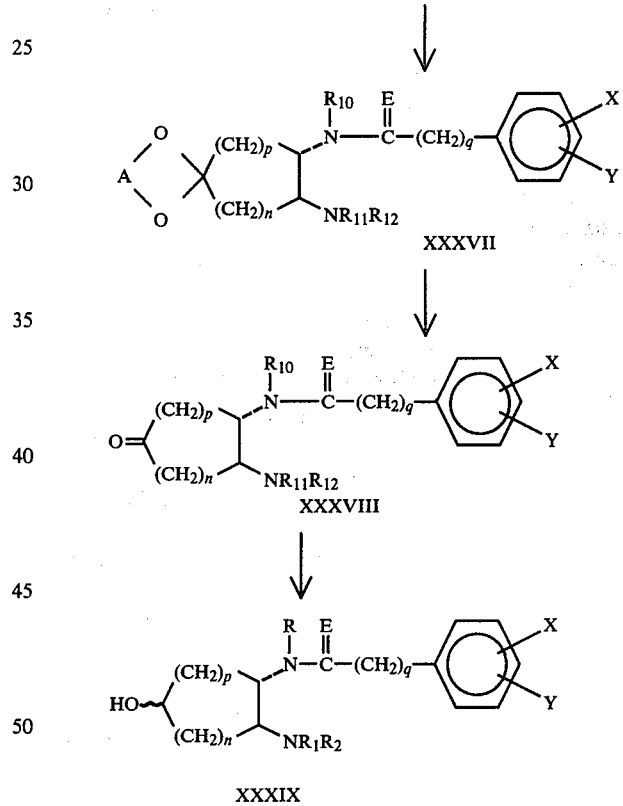
CHART D
(To prepare cis amino amides wherein p is zero)
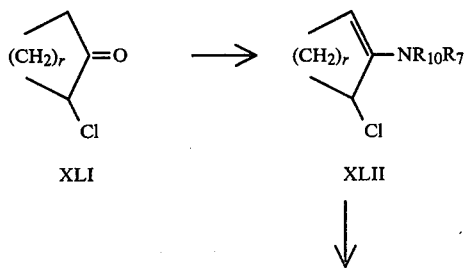

CHART D
-continued
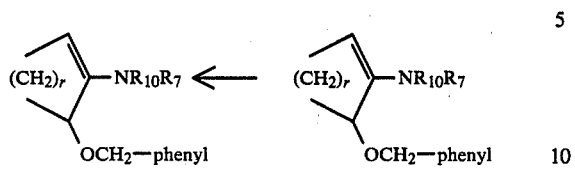
XLIV    XLIII
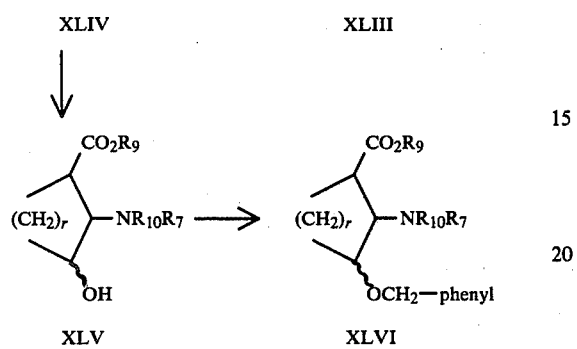
XLV    XLVI
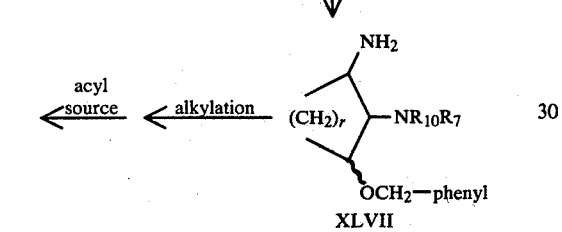
XLVII
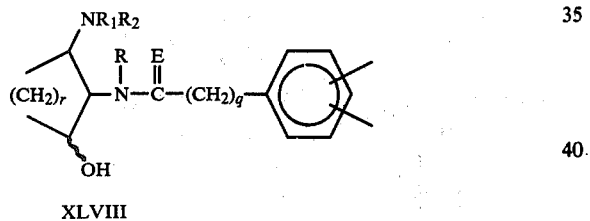
XLVIII
CHART E
(To prepare cis amino amides wherein n is zero)
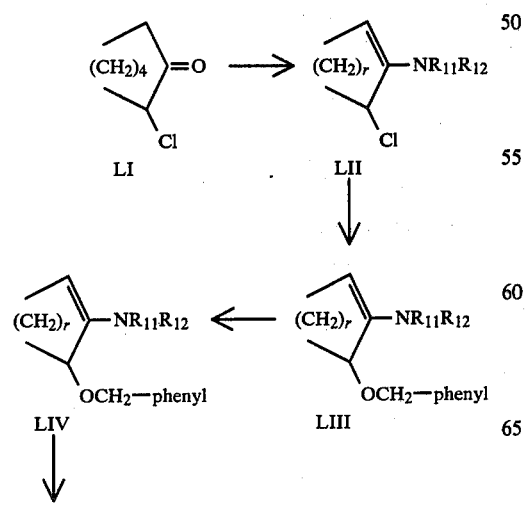
LI    LII
LIV    LIII
CHART E
(To prepare cis amino amides wherein n is zero)
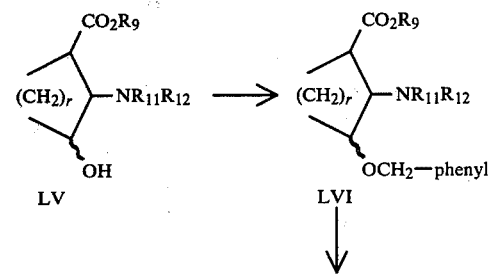
LV    LVI
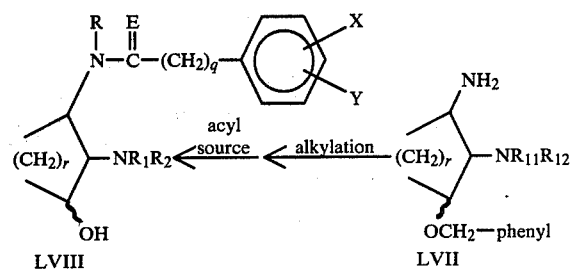
LVIII    LVII

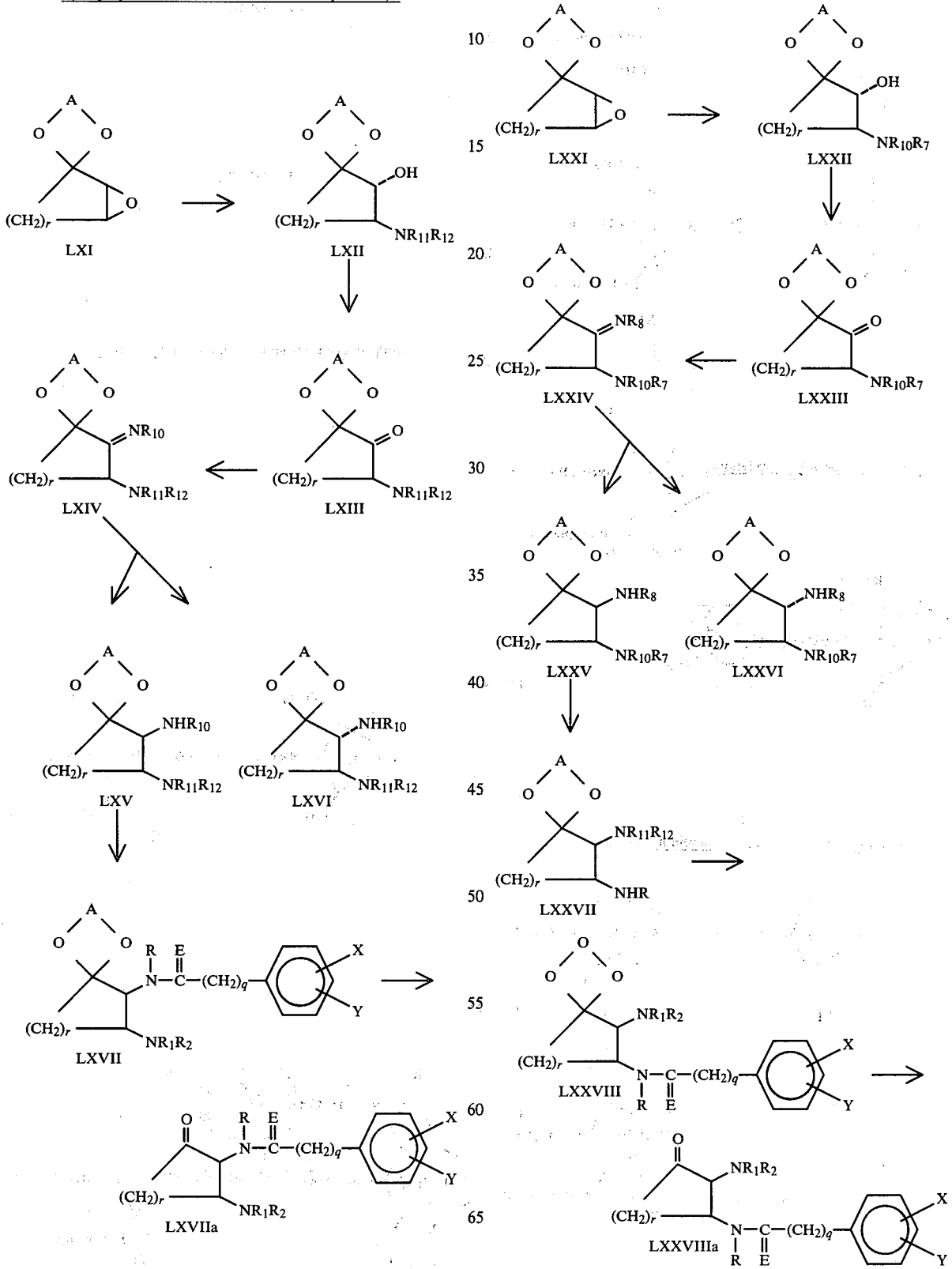

CHART H
(To prepare cis amino hydroxy and keto amides wherein p is zero)
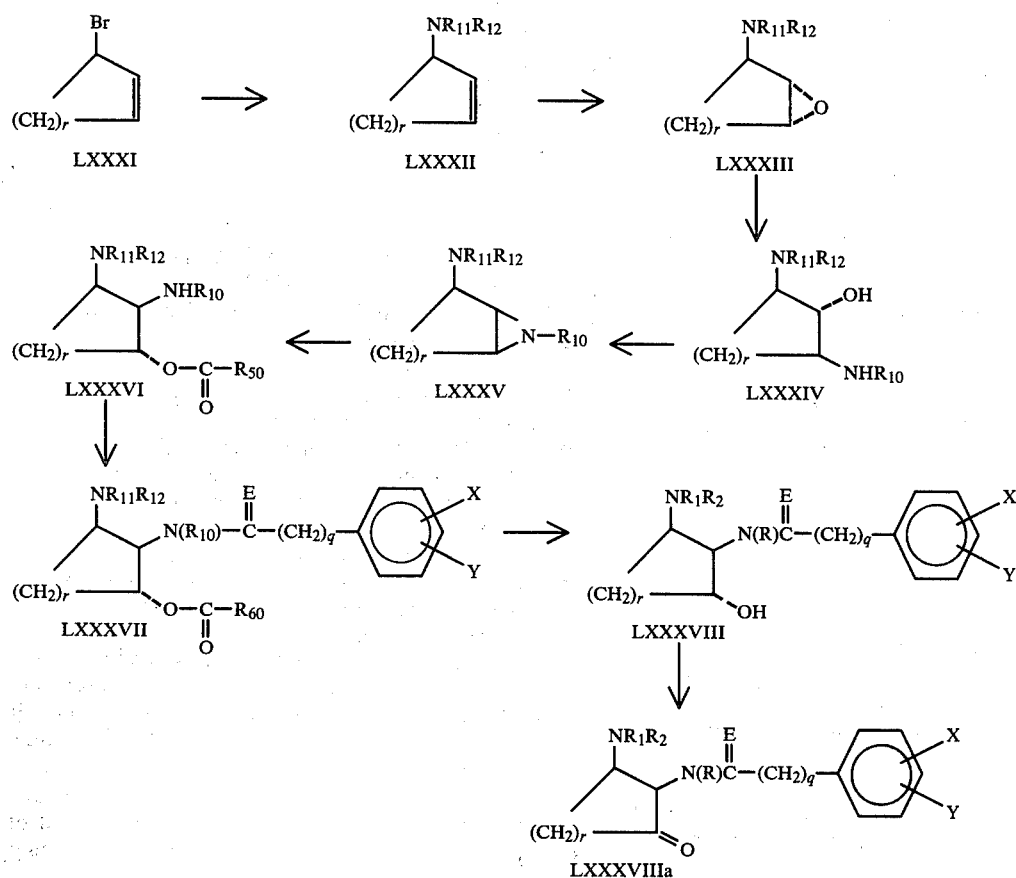
CHART I
(To prepare cis amino hydroxy and keto amides wherein n is zero)
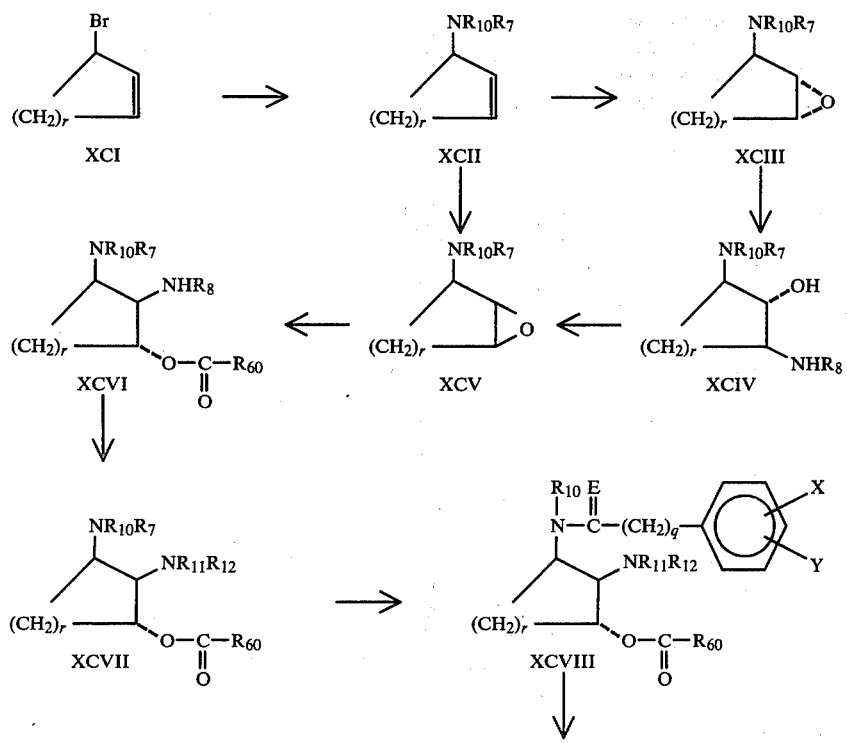

-continued
CHART I
(To prepare cis amino hydroxy and keto amides wherein n is zero)

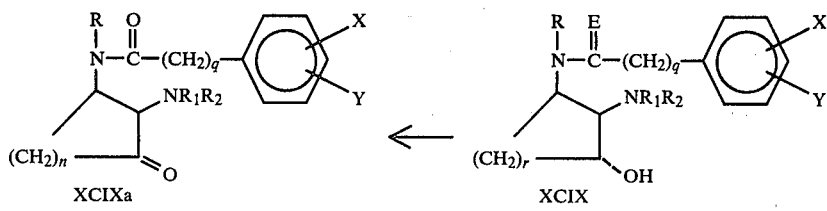

We claim:
1. A compound of the formula

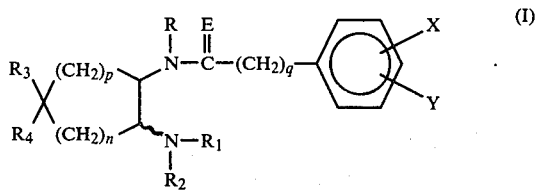

wherein
R is hydrogen or $C_1$ to $C_3$-alkyl;
$R_1$ and $R_2$, taken separately, are each hydrogen or $C_1$ to $C_3$-alkyl;
$R_1$ and $R_2$, taken together with the nitrogen to which they are bonded, are azetidinyl, pyrrolidinyl or piperidinyl;
$R_3$, taken separately, is hydrogen,
$R_4$, taken separately, is mercapto(—SH), —S($C_1$ to $C_3$-alkyl), or $R_3$ is —$GR_5$ when $R_4$ is —$GR_5$;
$R_5$ is $C_1$ to $C_2$-alkyl;
each G is oxygen or bivalent sulfur, and both G moieties are the same in any one compound;
X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino(—NHC(=O)$R_6$, wherein $R_6$ is halogen or $C_1$ to $C_2$-alkyl;
p and n are whole number integers selected from the group zero, 2, 3, or 4 such that one of p and n is zero and the other of p and n is 2, 3, or 4;
q is zero or 1;
E is oxygen or bivalent sulfur;
or a pharmaceutically acceptable salt thereof.
2. A compound according to claim 1 wherein one of p and n is 0, and the other of p and n is 2, 3 or 4, and p and n are selected so that the cycloaliphatic ring has 5 to 7 ring carbon atoms, q is 0 or 1;
at least one of X and Y is a halogen having an atomic number of from 9 to 35 in the 3- or 4-position of the phenyl ring, or both of X and Y are such a halogen in the 3- or 4-position of the phenyl ring;
R is $C_1$ to $C_3$-alkyl;
$R_1$ and $R_2$ are taken together with the nitrogen to which they are bonded to complete an azetidinyl, pyrrolidinyl or piperidinyl group;
E is oxygen;
$R_3$ and $R_4$ are each —$GR_5$, where each G is oxygen and $R_5$ is $C_1$ to $C_2$-alkyl;
or a pharmaceutically acceptable salt thereof.

3. A compound according to claim 2 which is 4-bromo-N-[3,3-dimethoxy-2-(1-pyrrolidinyl)cyclohexyl]-N-methylbenzamide, or a pharmacologically acceptable salt thereof.
4. A compound according to claim 3 which is ($\pm$)-(1$\alpha$,2$\beta$)-4-bromo-N-[3,3-dimethoxy-2-(1-pyrrolidinyl)cyclohexyl]-N-methylbenzeneacetamide, or a pharmacologically acceptable salt thereof.
5. A compound according to claim 2 which is 3,4-dichloro-N-[6,6-dimethoxy-2-(1-pyrrolidinyl)cyclohexyl]-N-methylbenzeneacetamide.
6. A compound according to claim 2 which is 4-bromo-N-[6,6-dimethoxy-2-(1-pyrrolidinyl)cyclohexyl]-N-methylbenzamide.
7. A composition useful in pharmaceutically effective dosage unit form for alleviating pain in warm-blooded mammals which comprises a compound of Formula I in claim 1 in combination with a pharmaceutically acceptable carrier.
8. A method of alleviating pain in a warm-blooded animal which comprises administering to an animal suffering pain an effective amount of a compound of claim 1 in a pharmaceutically acceptable dosage unit form.
9. A composition of claim 7 wherein the compound of Formula I is a compound of the structure

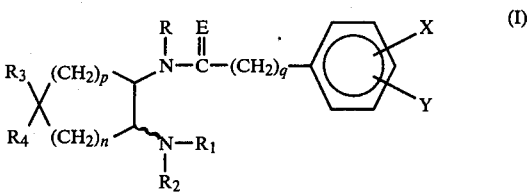

wherein one of p and n is 0, and the other of p and n is 2, 3 or 4, and p and n are selected so that the cycloaliphatic ring has 5 to 7 ring carbon atoms, q is 0 or 1;
at least one of X and Y is a halogen having an atomic number of from 9 to 35 in the 3- or 4-position of the phenyl ring, or both of X and Y are such a halogen in the 3- or 4-position of the phenyl ring;
R is $C_1$ to $C_3$-alkyl;
$R_1$ and $R_2$ are taken together with the nitrogen to which they are bonded to complete an azetidinyl, pyrrolidinyl or piperidinyl group;
E is oxygen;
$R_3$ and $R_4$ are each —$GR_5$, where each G is oxygen and $R_5$ is $C_1$ to $C_2$-alkyl;
or a pharmacologically acceptable salt thereof.
10. A composition of claim 7 wherein the compound of Formula I is 4-bromo-N-[3,3-dimethoxy-2-(1-pyrrolidinyl)cyclohexyl]-N-methylbenzamide, or a pharmacologically acceptable salt thereof.

* * * * *

UNITED STATES PATENT OFFICE
CERTIFICATE OF CORRECTION

Patent No. 4,460,600                Dated July 17, 1984

Inventor(s) LESTER J. KAPLAN ET AL

It is certified that error appears in the above-identified patent and that said Letters Patent are hereby corrected as shown below:

Column 14, line 41: ",isclosed" should read -- disclosed --.
Column 16, line 52: "MeOH-NH4OH-EtOAc" should read -- MeOH-NH$_4$OH-EtOAc --.
Column 19, line 33: "... 2-(lazetidinyl) ..." should read
    -- ... 2-(1-azetidinyl) ... --.
Column 19, line 37: "4-Azido-N- " should read -- h. 4-Azido-N- --.
Column 29, Chart H, Formula LXXXVI (part of formula) should read as
    follows:

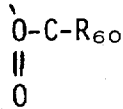

Column 31, Claim 1, line 45: "R$_6$ is halogen" should read --R$_6$ is
    hydrogen --.

Signed and Sealed this

Thirtieth Day of April 1985

[SEAL]

Attest:

DONALD J. QUIGG

Attesting Officer      Acting Commissioner of Patents and Trademarks